United States Patent
Weser et al.

(10) Patent No.: US 9,132,288 B2
(45) Date of Patent: *Sep. 15, 2015

(54) SUBSTANCE FOR DYEING KERATIN FIBERS, INCLUDING CATIONIC ANTHRAQUINONE DYES AND ANIONIC POLYMERS

(71) Applicant: Henkel AG & Co. KGaA, Düsseldorf (DE)

(72) Inventors: Gabriele Weser, Neuss (DE); Claudia Kolonko, Remscheid (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,825

(22) Filed: Jun. 18, 2014

(65) Prior Publication Data

US 2014/0289971 A1    Oct. 2, 2014

Related U.S. Application Data

(63) Continuation of application No. PCT/EP2012/073026, filed on Nov. 20, 2012.

(30) Foreign Application Priority Data

Dec. 20, 2011 (DE) .......... 10 2011 089 217

(51) Int. Cl.
| | | |
|---|---|---|
| *A61Q 5/10* | (2006.01) | |
| *A61K 8/73* | (2006.01) | |
| *A61K 8/35* | (2006.01) | |
| *A61Q 5/06* | (2006.01) | |
| *A61K 8/81* | (2006.01) | |
| *A61K 8/41* | (2006.01) | |
| *A61Q 5/08* | (2006.01) | |

(52) U.S. Cl.
CPC . *A61Q 5/10* (2013.01); *A61K 8/355* (2013.01); *A61K 8/416* (2013.01); *A61K 8/73* (2013.01); *A61K 8/731* (2013.01); *A61K 8/733* (2013.01); *A61K 8/8147* (2013.01); *A61K 8/8152* (2013.01); *A61K 8/8158* (2013.01); *A61K 8/8164* (2013.01); *A61Q 5/065* (2013.01); *A61Q 5/08* (2013.01); *A61K 2800/4322* (2013.01); *A61K 2800/5424* (2013.01)

(58) Field of Classification Search
CPC .......... A61Q 5/10; A61Q 5/065; A61Q 5/08; A61K 8/73; A61K 8/731; A61K 8/8147; A61K 8/8158; A61K 8/416; A61K 8/8152
USPC ............................. 8/405, 462, 557, 558, 643
See application file for complete search history.

(56) References Cited

FOREIGN PATENT DOCUMENTS

| CA | 2613049 | * | 4/2008 | ............... A61Q 5/10 |
|---|---|---|---|---|
| CA | 2613049 A1 | | 4/2008 | |
| DE | 1020090545569 A1 | * | 10/2010 | ............... A61K 8/97 |
| EP | 0815828 A1 | | 1/1998 | |
| EP | 1006154 B1 | | 6/2000 | |
| EP | 1820826 A1 | * | 8/2007 | ............... A61Q 5/10 |
| EP | 2329809 A1 | | 6/2011 | |
| WO | 9744004 A1 | | 11/1997 | |

OTHER PUBLICATIONS

STIC Search Report dated Aug. 26, 2014.*
English translation (Sep. 15, 2014) of the Patent No. DE 102009054569 A1.*
KH. Schrader: 'Grundlagen und Rezepturen der Kosmetika', (translation Basics and recipes of cosmetics), 2., verbesserte und erweiterte Auflage, 1989, Huthig Buch Verlag Heidelberg, pp. 1-20 (book table of contents), English abstract machine translation only.

* cited by examiner

Primary Examiner — Eisa Elhilo
(74) Attorney, Agent, or Firm — Steven L. Nichols; Van Cott, Bagley, Cornwall & McCarthy P.C.

(57) ABSTRACT

The present disclosure provides an agent for coloring keratinic fibers comprising, in a cosmetic carrier, (a) at least one compound of formula (I) and (b) at least one anionic polymer. The present disclosure also provides a method of using such an agent to produce increased shine, an intense color result with improved fastness properties, or reduced selectivity.

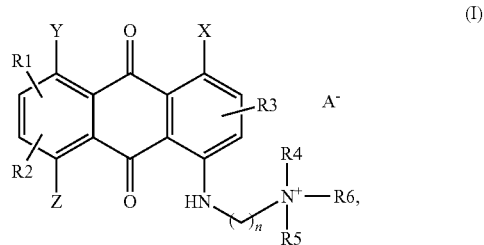

(I)

20 Claims, No Drawings

SUBSTANCE FOR DYEING KERATIN FIBERS, INCLUDING CATIONIC ANTHRAQUINONE DYES AND ANIONIC POLYMERS

RELATED DOCUMENTS

The present application claims the benefit and is a U.S. continuation patent application under 35 U.S.C. 111(a) and claims the right of priority under 35 U.S.C. 365 to international patent Application No. PCT/EP2012/073026, filed Nov. 20, 2012, entitled "Substance for Dyeing Kerating Fibers, Including Cationic Anthraquinone Dyes and Anionic Polymers" which claims benefit of German application No.: 102011089217.6, filed Dec. 20, 2011, these applications are herein incorporated by reference in their entirety.

FIELD OF THE INVENTION

The present specification relates generally to agents for coloring and optionally simultaneously lightening keratinic fibers. More specifically, the present application relates to cosmetic agents including cationic anthraquinone dyes and special anionic polymers. The present specification also relates to the use of these agents to produce hair colors having increased shine, an intense color result, improved fastness properties and reduced selectivity.

BACKGROUND OF THE INVENTION

As a general rule, either substantive dyes or oxidation dyes may be used for coloring keratinic fibers. Although intense colors with good fastness properties may be obtained with oxidation dyes, the development of the color generally takes place under the influence of oxidizing agents such as $H_2O_2$ for example, which in some cases may result in damage to the fiber. Furthermore, some oxidation dye precursors or certain mixtures of oxidation dye precursors may have a sensitizing effect on people with sensitive skin. Substantive dyes are applied under gentler conditions. The disadvantage of these dyes, however, lies in the fact that the colors often have inadequate fastness properties, in particular with regard to hair washing, but also with respect to external influences, such as sunlight, or reactive environmental chemicals, such as swimming pool water, for example.

For temporary colors, coloring or tinting agents are conventionally used which include substantive dyes as the coloring component. Substantive dyes are dye molecules which attach directly to the hair and do not require an oxidative process to develop the color. These dyes include henna, for example, which has been known since ancient times for coloring the body and hair. These colors are generally significantly more sensitive to shampooing than oxidative colors, such that an often undesired shift in shade or even a visible decolorization occurs much more quickly.

Achieving a uniform coloring of hair that has been frequently treated, such as for example bleached or permanently waved hair, where the fibers present differing degrees of pre-existing damage in the various lengths or variously treated areas, represents a particular challenge in terms of coloring hair with substantive dyes. During the coloring process itself, the coloring agent may exhibit uneven coloring on hair with differing degrees of pre-existing damage, while repeated hair washing may also cause the dyes to be washed out of the different areas of the hair to varying degrees, resulting in an inconsistent, and hence undesirable, color result.

In the development of coloring products based on substantive dyes, there is still a particular focus on producing dye formulations having reduced selectivity, meaning that a uniform color result may be achieved on sections of the hair that have varying degrees of pre-existing damage. In particular, this reduced selectivity should remain present not only immediately after the coloring process but also after repeated hair washes.

The object of the present specification is therefore to provide a coloring agent for keratinic fibers, in particular human hair, which, in addition to other positive fastness properties, has in particular a low selectivity (or a good equalizing capacity) and good wash fastness.

The colors achieved with the agents according to the present specification should deliver a brilliant and intense color result, both immediately after the coloring process and after repeated hair washes. Following application of the coloring agent, the hair should be uniformly colored, even in cases where the hair exhibits varying degrees of pre-existing damage, wherein this uniformity in the color result should still be present even after repeated hair washes.

In the present specification, an object was also to provide brilliant and neutral blue shades, or shades in the blue range, with the aforementioned advantageous fastness properties, said shades being extremely suitable for matting. The agents should additionally have an optimal viscosity, both with respect to the application process and the coloring capacity.

The use of cationic anthraquinone dyes in products for coloring keratinic fibers is already known in principle from the prior art, for example from EP 1 006 154 B1 or EP 1 820 826 A1. Furthermore, combinations of cationic anthraquinone dyes with oxidation dye precursors of the developer type are claimed in EP 2 329 809 for the oxidative coloring of hair.

Combinations of cationic anthraquinones with special anionic polymers have not yet been described.

During the course of the work leading to the agents of the present disclosure it was surprisingly found that these combinations lead to colors which achieve the above object to an outstanding degree.

Furthermore, other desirable features and characteristics of the present invention will become apparent from the subsequent detailed description of the invention and the appended claims, taken in conjunction with this background of the invention.

BRIEF SUMMARY OF THE INVENTION

The present specification firstly provides an agent for coloring (which may also simultaneously lighten) keratinic fibers comprising, in a cosmetic carrier,
(a) at least one compound of formula (I):

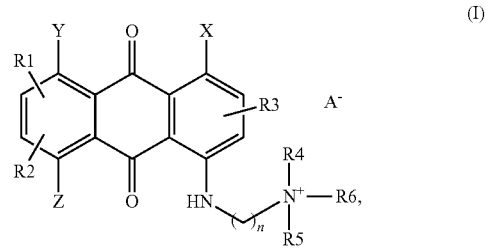

in which:

R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;

n denotes an integer between 2 and 6 inclusive; and $A^-$ denotes a physiologically acceptable anion;

and (b) at least one anionic polymer.

The present specification secondly provides a method of using a cosmetic agent for coloring keratinic fibers. The method comprises:

(A) applying an agent for coloring (which may also simultaneously lighten) keratinic fibers comprising, in a cosmetic carrier, (i) at least one compound of formula (I):

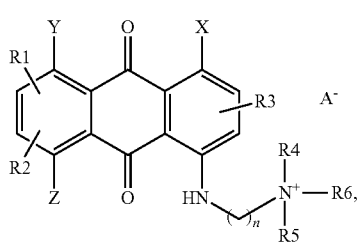

(I)

in which:

R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group; or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;

n denotes an integer between 2 and 6 inclusive; and $A^-$ denotes a physiologically acceptable anion;

and (ii) at least one anionic polymer; and (B) after a contact time, rinsing the agent from the keratinic fibers.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

According to the present specification, the terms "Keratin-containing fibers," "keratinic fibers," or similar terminology is understood to mean all animal hair, for example wool, horsehair, angora hair, fur, feathers and products or textiles manufactured therefrom. The keratinic fibers are, however, preferably human hair.

The term "coloring of keratin fibers," in the context of the present specification includes any form of color changing of fibers. It includes in particular the color changes covered by the terms tinting, lightening, bleaching, peroxiding, oxidative coloring, semipermanent coloring, permanent coloring and temporary coloring. It explicitly also includes color changes according to the present specification, which may present a lighter color result in comparison to the original color, such as for example, combined coloring and bleaching processes.

The agents according to the present specification include the cationic anthraquinone(s) of formula (I) and the anionic polymer(s) in a cosmetic carrier, preferably in a suitable aqueous, alcoholic or aqueous-alcoholic carrier. For the purposes of hair coloring such carriers are for example creams, emulsions, gels or surfactant-containing foaming solutions, such as for example shampoos, foam aerosols, foam formulations or other preparations which are suitable for use on the hair. It is also possible, however, for the agents according to the present specification to be integrated into a formulation in powder or tablet form.

In the context of the present specification aqueous-alcoholic solutions are understood to be aqueous solutions including 3 to 70 weight percent (wt. %) of a $C_1$ to $C_4$ alcohol, in particular ethanol or isopropanol. The agents according to the present specification may additionally include further organic solvents, such as for example methoxybutanol, benzyl alcohol, ethyl diglycol or 1,2-propylene glycol. All water-soluble organic solvents are preferred here.

The first essential ingredient (a) of the agents according to the present specification is at least one substantive cationic anthraquinone dye of the general formula (I):

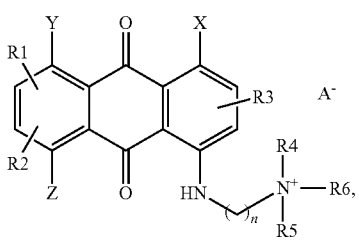

(I)

The substituents R1 to R8 of the compound of formula (I) are described below by way of non-limiting examples: Examples of a $C_1$-$C_6$ alkyl group are the methyl, ethyl, propyl, isopropyl, n-butyl, s-butyl and t-butyl, n-pentyl and n-hexyl groups. Propyl, ethyl and methyl are preferred alkyl residues. Examples of a $C_2$-$C_6$ alkenyl group are vinyl, allyl, but-2-enyl, but-3-enyl and isobutenyl, preferred $C_2$-$C_6$ alkenyl residues being vinyl and allyl. Preferred examples of a $C_1$-$C_6$ hydroxyalkyl group are a hydroxymethyl, 2-hydroxyethyl, 2-hydroxypropyl, 3-hydroxypropyl, 4-hydroxybutyl, 5-hydroxypentyl and 6-hydroxyhexyl group; a 2-hydroxyethyl group is particularly preferred. $C_1$-$C_6$ alkoxy groups that are preferred according to the present specification are the methoxy or ethoxy group. Examples of halogen atoms are F, Cl, Br or I atoms, with Br or Cl atoms being most particularly preferred. Preferred examples of $C_1$-$C_6$ alkoxy $C_2$-$C_6$ alkyl groups are the methoxyethyl, ethoxyethyl, methoxypropyl, methoxybutyl, ethoxypropyl, ethoxybutyl and methoxyhexyl group. Examples of a $C_1$-$C_6$ acyl amino group are the acetamide group, the propanamide group and the butanamide group, the acetamide group being preferred. The pyrrolidinium ring, the piperidinium ring, the morpholinium ring and the 1-azepanium ring may be mentioned as preferred examples of a 5-, 6- or 7-membered ring formed from R4, R5 and the quaternary nitrogen atom.

Dyes of formula (I) in which R1, R2 and R3, independently of one another, denote hydrogen, halogen, a carboxyl group, a sulfonic acid group, a $C_1$-$C_6$ alkyl group or a $C_1$-$C_6$ alkoxy group deliver particularly intense color results, and are therefore preferred.

It is furthermore preferable for one of the residues selected from R1, R2 and R3 to denote halogen, a carboxyl group, a sulfonic acid group, a $C_1$-$C_6$ alkyl group or a $C_1$-$C_6$ alkoxy group and for the other two residues selected from R1, R2 and R3 both to denote hydrogen.

A preferred example is an agent for coloring and optionally simultaneously lightening keratinic fibers, which is characterized in that it includes a compound of formula (I) in which at least one of the residues R1, R2 and/or R3 denotes a $C_1$-$C_6$ alkyl group.

In the case of particularly suitable compounds of formula (I), one of the residues selected from R1, R2 and R3 denotes a $C_1$-$C_6$ alkyl group and the other two residues selected from R1, R2 and R3 denote hydrogen.

In a most particularly preferred example R1 and R2 both denote a hydrogen atom and R3 denotes a methyl group.

Furthermore, particularly good coloring results are obtained with agents including at least one compound of formula (I) in which the residues R4, R5 and R6, independently of one another, denote a $C_1$-$C_6$ alkyl group or an alkenyl group. In particular, each of the residues R4, R5 and R6 preferably denotes a $C_1$-$C_6$ alkyl group.

It is most particularly preferable for R4 and R5 both to denote a methyl group and for R6 to denote a methyl group, an ethyl group or an n-propyl group.

It is also most particularly preferable for R4 and R5 both to denote a methyl group and for R6 to denote an n-propyl group.

In a likewise particularly preferred example, the residues R4, R5 and R6 each denote a methyl group.

For compounds of formula (I) there is the proviso that at least one of the residues X, Y and Z denotes an N(R7)(R8) group. Colors having good application properties were obtained in particular when compounds of formula (I) were used in which X denotes an N(R7)(R8) group and Y and Z each denote hydrogen.

R7 and R8, preferably (and independently of one another) denote hydrogen or a $C_1$-$C_6$ alkyl group. R7 and R8 particularly preferably (also independently of one another) denote hydrogen or a methyl group. Compounds of formula (I) in which both R7 and R8 denote hydrogen have proved to be particularly suitable and are therefore particularly preferred.

In the context of the work leading to the agents of the present disclosure, it has also proved most particularly advantageous for X to denote an $NH_2$ group.

A further preferred example is therefore an agent for coloring and optionally simultaneously lightening keratinic fibers, which is characterized in that it includes a compound of formula (I) in which at least X denotes an $NH_2$ group.

n preferably denotes the numbers 2 or 3 and most particularly preferably the number 3.

$A^-$ denotes a physiologically acceptable anion. Suitable physiologically acceptable anions are halide, hydrogen sulfate, ½ sulfate, benzene sulfonate, p-toluene sulfonate, acetate, citrate, lactate, ½ tartrate, methosulfate ($H_3COSO_3^-$) or trifluoromethane sulfonate. $A^-$ particularly preferably denotes bromide or methosulfate ($H_3COSO_3^-$), with $A^-$ most particularly preferably denoting methosulfate ($H_3COSO_3^-$).

Agents for coloring, and optionally simultaneously lightening, keratinic fibers that are preferred according to the present specification are characterized in that they include at least one compound of the general formula (I) selected from 3-[(4-amino-9,10-dihydro-3-methyl-9,10-dioxo-1-anthracenyl)amino]-N,N,N-trimethyl-1-propanaminium methosulfate, 3-[(4-amino-9,10-dihydro-3-methyl-9,10-dioxo-1-anthracenyl)amino]-N,N,N-trimethyl-1-propanaminium bromide, 3-[(4-amino-9,10-dihydro-3-methyl-9,10-dioxo-1-anthracenyl)amino]-N,N,N-trimethyl-1-propanaminium chloride, 3-[(4-amino-9,10-dihydro-3-methyl-9,10-dioxo-1-anthracenyl)amino]-N,N,N-trimethyl-1-propanaminium-p-toluenesulfonate, 3-[(4-amino-9,10-dihydro-3-methyl-9,10-dioxo-1-anthracenyl)amino]-N,N,N-trimethyl-1-propanaminium acetate, 3-{[9,10-dihydro-4-(methylamino)-9,10-dioxo-1-anthracenyl]amino}-N,N-dimethyl-N-propyl-1-propanaminium methosulfate, 3-{[9,10-dihydro-4-(methylamino)-9,10-dioxo-1-anthracenyl]amino}-N,N-dimethyl-N-propyl-1-propanaminium bromide, 3-{[9,10-dihydro-4-(methylamino)-9,10-dioxo-1-anthracenyl]amino}-N,N-dimethyl-N-propyl-1-propanaminium chloride, 3-{[9,10-dihydro-4-(methylamino)-9,10-dioxo-1-anthracenyl]amino}-N,N-dimethyl-N-propyl-1-propanaminium-p-toluenesulfonate and 3-{[9,10-dihydro-4-(methylamino)-9,10-dioxo-1-anthracenyl]amino}-N,N-dimethyl-N-propyl-1-propanaminium acetate.

The compound of formula (Ia) has proved to be an ideally suitable compound of formula (I) for achieving the object according to the present specification,

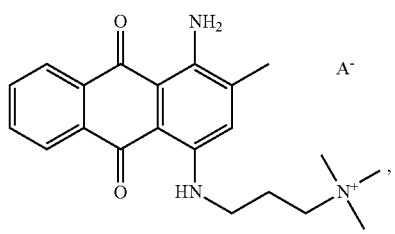

in which A⁻ denotes a physiologically acceptable anion, preferably methosulfate ($H_3COSO_3^-$).

A further particularly preferred example is therefore an agent for coloring and optionally simultaneously lightening keratinic fibers, which is characterized in that it includes as the compound of formula (I) the compound according to formula (Ia),

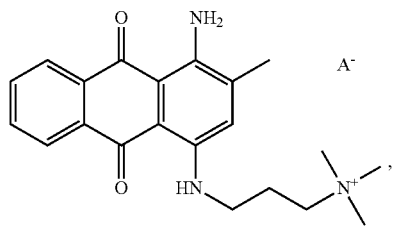

in which A⁻ denotes a physiologically acceptable anion, preferably methosulfate ($H_3COSO_3^-$).

The agents according to the present specification for coloring, and optionally simultaneously lightening, keratin fibers include the compound(s) of formula (I) preferably in amounts above 0.0001 wt. % and below 5 wt. %, relative in each case to the total agent.

A preferred example is an agent which includes the compound(s) of formula (I) in an amount of from 0.0001 to 5 wt. %, preferably from 0.005 to 3.5 wt. %, particularly preferably from 0.01 to 2.5 wt. %, in particular from 0.05 to 1.5 wt. %, and in particular preferably from 0.01 to 1.0 wt. %, relative in each case to the total weight of the agent.

As the second essential constituent of the formulation (b), the agents according to the present specification include at least one anionic polymer.

An anionic polymer is understood according to the present specification to be a polymer which under standard conditions in a protic solvent, in particular in an aqueous environment, bears structural units having anionic groups. These anionic groups are neutralized using stoichiometric equivalents of counterions, such as for example alkali metal cations, alkaline-earth metal cations or ammonium ions ($NH_4^+$), in order to obtain electroneutrality. The anionic functional groups present in the polymer may include carboxyl groups, sulfonic acid groups and phosphonic acid groups, in particular carboxyl and sulfonic acid groups. When the polymer is used, the carboxylic acid and sulfonic acid groups may also initially still be in protonated (uncharged) form and may then be converted to the corresponding anionic form by removal of a proton on contact with the aqueous environment.

In a preferred example, the anionic polymer (b) is selected from
(i) polymers of acrylic acid, methacrylic acid, or combinations thereof;
(ii) polymers of 2-acrylamido-2-methyl-1-propanesulfonic acid;
(iii) anionic polysaccharides;
(iv) polymers of itaconic acid;
(v) polymers of crotonic acid;
(vi) polymers of maleic anhydride; and
(vii) combinations thereof.

A further preferred example is therefore an agent for coloring and optionally simultaneously lightening keratinic fibers, which is characterized in that as the anionic polymer (b) it includes a polymer selected from
(i) polymers of acrylic acid, methacrylic acid, or combinations thereof;
(ii) polymers of 2-acrylamido-2-methyl-1-propanesulfonic acid;
(iii) anionic polysaccharides;
(iv) polymers of itaconic acid;
(v) polymers of crotonic acid;
(vi) polymers of maleic anhydride; and
(vii) combinations thereof.

In one example, the agents according to the present specification may include as the anionic polymer (b) at least (i) one polymer of acrylic acid and/or methacrylic acid. The definition of polymer includes both homopolymers and copolymers of acrylic acid and/or methacrylic acid. Homopolymers are by definition polymers produced from monomers of just one type. By contrast, copolymers are synthesized from a plurality of different monomers.

The homopolymers and copolymers of type (i) are characterized in that they include at least one structural unit of formula (P-I):

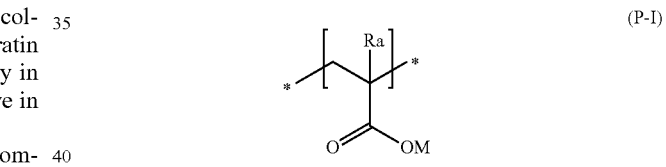

in which:
Ra denotes a hydrogen atom or a methyl group and
M denotes a hydrogen atom or sodium, potassium, ½ magnesium or ½ calcium.

A preferred homopolymer is polyacrylic acid, such as may be obtained for example from 3V Sigma under the trade name Synthalen® K or Synthalen M or from Lubrizol under the trade name Carbopol® (for example Carbopol® 980, 981, 954, 2984 and 5984), with the INCI name Carbomer in each case. The product sold by BASF under the trade name Cosmedia® SP (INCI name: SODIUM POLYACRYLATE) may also be mentioned in this context as a preferred acrylic acid homopolymer.

The sodium acrylate/sodium acryloyldimethyl taurate copolymers sold under the name Simulgel® EG as a compound with isohexadecane and polysorbate-80 (INCI name: SODIUM ACRYLATE/SODIUM ACRYLOYLDIMETHYL TAURATE COPOLYMER, ISOHEXADECANE, POLYSORBATE 80) have also proved particularly effective according to the present specification.

At least one copolymer of acrylic acid and/or methacrylic acid may also be used as the anionic polymer. A suitable polymer in this context is the polymer known under the INCI name Acrylates/C10-30 Alkyl Acrylate Crosspolymer, which is available from Noveon under the trade name Carbopol® 1382. A further suitable polymer is the polymer known under the INCI name Acrylates/Steareth-20 Methacrylate Crosspolymer, which is sold for example under the trade name Aculyn® 88 by Rohm & Haas in the form of a 28 to 30 wt. % dispersion in water. Polymers known under INCI nomenclature as Acrylates/Palmeth-25 Acrylate Copolymer or Acrylates/Palmeth-20 Acrylate Copolymer may also be used. Such polymers are available for example from 3V Sigma under the trade name Synthalen® W 2000 as a 30 to 32 wt. % emulsion in water.

Within this example it may likewise be preferable to use a copolymer consisting of at least one anionic acrylic acid or methacrylic acid monomer and at least one non-ionogenic monomer. Preferred non-ionogenic monomers in this context are acrylamide, methacrylamide, acrylic acid ester, methacrylic acid ester, vinylpyrrolidone, vinyl ether and vinyl ester.

Further preferred anionic copolymers are, for example, copolymers of acrylic acid and/or methacrylic acid and the $C_1$-$C_6$ alkyl esters thereof, such as are sold under the INCI name Acrylates Copolymers. A preferred commercial product is, for example, Aculyn® 33 from Rohm & Haas. Also preferred, however, are copolymers of acrylic acid and/or methacrylic acid, the $C_1$-$C_6$ alkyl esters of acrylic acid and/or methacrylic acid and the esters of an ethylenically unsaturated acid and an alkoxylated fatty alcohol. Suitable ethylenically unsaturated acids are in particular acrylic acid, methacrylic acid and itaconic acid; suitable alkoxylated fatty alcohols are in particular Steareth-20 or Ceteth-20. Such copolymers are sold by Rohm & Haas under the trade name Aculyn® 22 (INCI name: Acrylates/Steareth-20 Methacrylate Copolymer).

Further preferred anionic acrylic acid or methacrylic acid copolymers are acrylic acid-acrylamide copolymers.

In a further preferred example, the agent for coloring, and optionally simultaneously lightening, keratinic fibers includes as the anionic polymer (b) exclusively at least one homopolymer and/or copolymer of acrylic acid and/or methacrylic acid.

A further preferred example is an agent for coloring and optionally simultaneously lightening keratinic fibers, which is characterized in that it includes as the anionic polymer (b) at least (i) one polymer of acrylic acid and/or methacrylic acid, which is preferably selected from the substances known under the INCI names Carbomer (polyacrylic acid),
Sodium Polyacrylate,
Sodium Acrylate/Sodium Acryloyldimethyl Taurate Copolymer,
Acrylates/C10-30 Alkyl Acrylate Crosspolymer,
Acrylates/Steareth-20 Methacrylate Crosspolymer,
Acrylates/Palmeth-25 Acrylate Copolymer,
Acrylates/Palmeth-20 Acrylate Copolymer,
Acrylates Copolymers,
Acrylates/Steareth-20 Methacrylate Copolymer, and combinations thereof.

In a further example, the agents according to the present specification may include as the anionic polymer (b) at least one (ii) polymer of 2-acrylamido-2-methyl-1-propanesulfonic acid. Among the polymers of this category the present specification likewise includes the homopolymers and copolymers of 2-acrylamido-2-methyl-1-propanesulfonic acid.

Polymers of type (ii) are characterized in that they include at least one structural unit of formula (P-II):

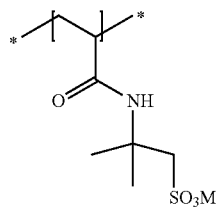

(P-II)

in which:
M denotes a hydrogen atom or sodium, potassium, ½ magnesium or ½ calcium.

Polymers of this type have anionic sulfonic acid functional groups, which are introduced into the polymer by polymerization of the monomer 2-methyl-2-[(1-oxo-2-propenyl)amino]-1-propanesulfonic acid (AMPS). Anionic homopolymers which include as the sole monomer 2-methyl-2[(1-oxo-2-propenyl)amino]-1-propanesulfonic acid (AMPS), in which some or all of the sulfonic acid group may be present as the sodium, potassium, ammonium, mono- or triethanolammonium salt, have proved to be most particularly effective.

Homopolymers of 2-methyl-2[(1-oxo-2-propenyl)amino]-1-propanesulfonic acid are very suitable for use in the agents according to the present specification. The compounds disclosed in the application EP 0815828 A1, the polymer known under the name Cosmedia® HSP 1160 and the product that is commercially available under the name Rheothik®11-80 may be mentioned as particularly suitable substances.

Polymers that are obtained by copolymerization of the 2-methyl-2[(1-oxo-2-propenyl)amino]-1-propanesulfonic acid building block with further monomers are likewise included in and preferred by the present specification.

A particularly preferred anionic copolymer consists of 70 to 55 molar percent (mol %) of acrylamide and 30 to 45 mol % of 2-acrylamido-2-methylpropane sulfonic acid, wherein some or all of the sulfonic acid group may be present as the sodium, potassium, ammonium, mono- or triethanolammonium salt. This copolymer may also be crosslinked, wherein polyolefinically unsaturated compounds such as tetraallyl oxyethane, allyl sucrose, allyl pentaerythritol and methylene bisacrylamide are preferably used as crosslinking agents.

Further preferred sulfonic acid polymers of this type are copolymers of 2-methyl-2[(1-oxo-2-propenyl)amino]-1-propanesulfonic acid (AMPS) and sodium acrylate, which are available from Seppic for example as the commercial product Simulgel® EG (INCI name: Sodium Acrylates/Sodium Acryloyldimethyl Taurate Copolymer, Isohexadecane, Polysorbate 80).

It may also be preferable for the agent for coloring, and optionally simultaneously lightening, keratinic fibers to include as the anionic polymer (b) exclusively at least one homopolymer and/or copolymer of 2-acrylamido-2-methyl-1-propanesulfonic acid.

In a further example the agents according to the present specification may include as the anionic polymer (b) at least one (iii) anionic polysaccharide. The group of (iii) anionic polysaccharides includes xanthans, alginates, carboxylalkyl celluloses and hyaluronic acids.

Xanthan is an anionic polysaccharide which is synthesized inter alia from the structural constituents D-glucose, D-mannose, D-glucuronic acid, acetate and pyruvate and which is also known under the INCI name Xanthan Gum.

Alginates (INCI name Algin) refer to the salts of alginic acid. Alginates are anionic polysaccharides including carboxyl groups and consisting of D-mannuronic acid and D-guluronic acid in varying proportions, which are linked by means of 1,4-glycoside bonds. Both the alkali and alkaline-earth salts of alginic acids are suitable according to the present specification.

The use of alginic acid, sodium alginate, potassium alginate, ammonium alginate and/or calcium alginate has proved particularly advantageous in the agents according to the present specification.

Carboxyalkyl celluloses are cellulose ethers in which the hydrogen atoms of the hydroxyl groups of the cellulose are substituted wholly or in part by carboxyalkyl groups. A preferred carboxyalkyl cellulose is carboxymethylcellulose, which may preferably be used as an anionic polymer in the form of its sodium salt (sodium carboxymethylcellulose).

The basic building block of hyaluronic acid (INCI name Hyaluronic acid, Sodium Hyaluronate) is an amino disaccharide synthesized from D-glucuronic acid and N-acetyl glucosamine in a 1,3-glycoside bond, which is bound to the next unit by β-1,4-glycoside. In the context of the work leading to the agents of the present disclosure, sodium and potassium salts of hyaluronic acid have proved to be particularly suitable for producing dye formulations that provide intense colorations with optimized viscosity.

It may be preferable in this context for the agent for coloring, and optionally simultaneously lightening, keratinic fibers to include as the anionic polymer (b) exclusively one or more anionic polysaccharides.

A further preferred example is an agent for coloring, and optionally simultaneously lightening, keratinic fibers that is characterized in that as the anionic polymer (b) it includes at least (iii) one anionic polysaccharide, preferably selected from
- xanthan (xanthan gum),
- alginate (algin),
- carboxymethylcellulose and/or the physiologically acceptable salts thereof,
- hyaluronic acid and/or the physiologically acceptable salts thereof, and/or
- combinations thereof.

In a further example, the agents according to the present specification may include as the anionic polymer (b) at least one (iv and/or v) polymer of itaconic acid and/or crotonic acid. Both the homopolymers and copolymers of itaconic acid and/or crotonic acid are included by the present specification. Polymers of this type are characterized in that they include as structural constituents at least one unit of formula (P-III) and/or of formula (P-IV):

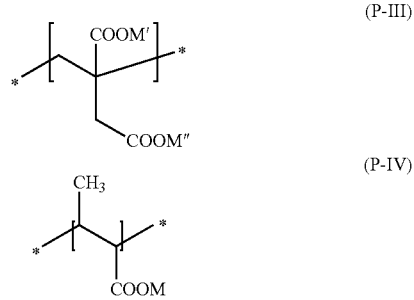

in which:
M, M', M'' each independently of one another, denotes a hydrogen atom or sodium, potassium, ½ magnesium or ½ calcium.

A preferred copolymer belonging to this class is for example the terpolymer which may be produced by copolymerization of vinyl chloride, vinyl acetate and itaconic acid and which is also commercially available from Wacker Polymer Systems under the trade name Vinnol® E 15/45 M.

It may also be preferable for the agent for coloring, and optionally simultaneously lightening, keratinic fibers to include as the anionic polymer (b) exclusively (iv and/or v) one or more homopolymers and/or copolymers of itaconic acid and/or crotonic acid.

In a further example, the agents according to the present specification may include as the anionic polymer (b) at least one (vi) polymer of maleic anhydride. This group includes homopolymers and copolymers including at least one structural unit of formula (P-V), which is formed by the polymerization and hydrolysis of the maleic anhydride monomer building block:

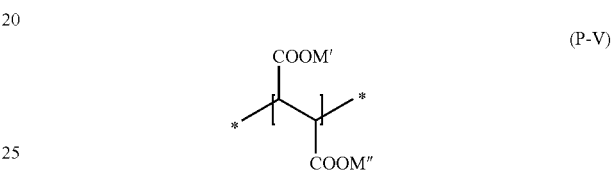

in which:
M', M'' independently of one another, denote a hydrogen atom or sodium, potassium, ½ magnesium or ½ calcium.

Preferred anionic polymers in this context are copolymers of maleic anhydride and methyl vinyl ether, in particular those having cross-linkages. A maleic acid-methyl vinyl ether copolymer crosslinked with 1,9-decadiene is available commercially under the name Stabileze® QM.

Finally it may be preferable for the agent for coloring and optionally simultaneously lightening keratinic fibers to include as the anionic polymer (b) exclusively (vi) one or more homopolymers and/or copolymers of maleic anhydride.

It is preferable for the agent according to the present specification to include at least one anionic polymer (b) selected from
(i) polymers and copolymers of acrylic acid, methacrylic acid, and/or combinations thereof,
(ii) polymers and copolymers of 2-acrylamido-2-methyl-1-propanesulfonic acid and/or
(iii) anionic polysaccharides.

The coloring agents that may be produced using these polymers or polymer combinations are exceptionally suitable for the object according to the present specification.

It is also particularly preferable for the agent according to the present specification to include at least one anionic polymer (b) selected from
(i) polymers and copolymers of acrylic acid, methacrylic acid, and/or combinations thereof.
(ii) polymers and copolymers of 2-acrylamido-2-methyl-1-propanesulfonic acid,
because dye formulations with optimized viscosity and particularly intense coloring properties may be obtained through the addition of these compounds or combinations thereof.

It is likewise most particularly preferable for the agent according to the present specification to include at least one anionic polymer (b) selected from
(i) polymers and copolymers of acrylic acid, methacrylic acid, and/or combinations thereof,
(iii) anionic polysaccharides, because dye formulations which are intensely coloring and provide particularly shiny colors may be obtained with the presence of these polymers or combinations thereof in the dye formulations.

The agents according to the present specification for coloring, and/or lightening, keratinic fibers include the anionic polymer(s) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent.

A further preferred example is therefore an agent for coloring, and optionally simultaneously lightening, keratinic fibers, which is characterized in that it includes the anionic polymer(s) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent.

In a further preferred example the agents according to the present specification additionally include, in addition to the compound of formula (I), at least one further substantive dye. Substantive dyes may be divided into anionic, cationic and non-ionic substantive dyes. The substantive dyes are preferably selected from nitrophenylenediamines, nitroaminophenols, azo dyes, anthraquinones, triarylmethane dyes or indophenols and physiologically acceptable salts thereof. The additional substantive dyes are each preferably used in a proportion from 0.001 to 2 wt. %, relative to the total application preparation.

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes including a heterocyclic compound having at least one quaternary nitrogen atom, in particular Basic Yellow 87, Basic Orange 31 and Basic Red 51. The cationic substantive dyes which are sold under the ARIANOR® trademark are likewise preferred cationic substantive dyes according to the present specification.

Non-ionic nitro and quinone dyes and neutral azo dyes in particular are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Coloring results with outstanding color intensity, brilliance and good wash fastness are obtained in particular if the agents according to the present specification include as the further substantive dye at least one dye selected from D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxethyl)-4-methyl-2-nitroaniline (Methyl Yellow), HC Yellow No. 2, Red B 54 and 2-amino-6-chloro-4-phenol.

The agents according to the present specification may also be used as oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are selected from at least one compound from the group formed from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof.

Particularly suitable oxidation dye precursors of the coupler type are selected from the group formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

The substantive dyes, developer components and coupler components are preferably each used in an amount of from 0.0001 to 5.0 wt. %, preferably from 0.001 to 2.5 wt. %, relative in each case to the ready-to-use agent. Developer components and coupler components may be used in approximately molar amounts to one another. Although the molar use has proved convenient, a certain excess of individual oxidation dye precursors is not disadvantageous, such that developer components and coupler components may be in a molar ratio of 1 to 0.5 to 1 to 3, in particular 1 to 1 to 1 to 2.

In the case of oxidation coloring agents the agents preferably include an oxidizing agent, preferably hydrogen peroxide. The amounts of hydrogen peroxide correspond to the amounts in the lightening agents according to the present specification.

The coloring agents may also be used as lightening coloring agents. In order to achieve the lightening effect, the agents include hydrogen peroxide and/or one of the solid addition products thereof with organic or inorganic compounds.

A further example of the first subject matter of the present specification is therefore characterized in that the agent additionally includes hydrogen peroxide and/or one of the solid addition products thereof with organic or inorganic compounds.

In a preferred example, hydrogen peroxide itself is preferably used as an aqueous solution. The concentration of a hydrogen peroxide solution in the agent according to the present specification is determined on the one hand by legal requirements and on the other by the desired effect; 6 to 12 wt. % solutions in water are preferably used. Ready-to-use agents of the first subject matter of the present specification that are preferred according to the present specification are characterized in that they include an amount of from 0.5 to 20 wt. %, preferably from 1 to 12.5 wt. %, particularly preferably from 2.5 to 10 wt. % and in particular from 3 to 6 wt. % of hydrogen peroxide, relative in each case to the total weight of the ready-to-use agent.

In order to achieve a stronger lightening and bleaching effect, the agent may also include at least one peroxo salt. Suitable peroxo salts are inorganic peroxo compounds, preferably selected from the group formed from ammonium peroxodisulfate, alkali metal peroxodisulfates, ammonium peroxomonosulfate, alkali metal peroxomonosulfates, alkali metal peroxodiphosphates and alkaline-earth metal peroxides. Peroxodisulfates are particularly preferred, in particular ammonium peroxodisulfate, potassium peroxodisulfate and sodium peroxodisulfate.

The persulfates are each included in the agent according to the present specification in an amount of from 0.5 to 20 wt. %, preferably from 1 to 12.5 wt. %, particularly preferably from 2.5 to 10 wt. % and in particular from 3 to 6 wt. %, relative to the total weight of the ready-to-use agent.

A further preferred example is an agent for coloring, and simultaneously lightening, keratinic fibers that additionally includes hydrogen peroxide, one of the solid addition products thereof with organic or inorganic compounds, ammonium peroxodisulfate, potassium peroxodisulfate and/or sodium peroxodisulfate, each in an amount of from 0.5 to 20 wt. %, preferably from 1 to 12.5 wt. %, particularly preferably from 2.5 to 10 wt. % and in particular from 3 to 6 wt. %, relative to the total weight of the ready-to-use agent.

To further increase the lightening, at least one $SiO_2$ compound such as silicic acid or silicates, in particular water glasses, may additionally be added to the composition according to the present specification. It may be preferable according to the present specification to use the $SiO_2$ compounds in an amount of from 0.05 wt. % to 15 wt. %, particularly preferably in an amount of from 0.15 wt. % to 10 wt. % and most particularly preferably in an amount of from 0.2 wt. % to 5 wt. %, relative in each case to the composition according to the present specification. The specified amounts indicate the content of $SiO_2$ compounds (excluding their water component) in the agents.

The ready-to-use coloring agents may also include additional active ingredients, auxiliary substances and additives to improve the coloring capacity and to establish further desired properties of the agents.

The ready-to-use coloring agents are preferably provided as a liquid preparation and therefore a surface-active substance is additionally added to the agents, such surface-active substances being referred to as surfactants or emulsifiers, depending on the field of application. They are preferably selected from anionic, cationic, zwitterionic, amphoteric and non-ionic surfactants and emulsifiers.

Agents that are preferred according to the present specification are characterized in that the agent additionally includes at least one anionic surfactant. Preferred anionic surfactants are fatty acids, alkyl sulfates, alkyl ether sulfates and ether carboxylic acids with 10 to 20 carbon atoms in the alkyl group and up to 16 glycol ether groups in the molecule. The anionic surfactants are used in an amount of from 0.1 to 45 wt. %, preferably from 1 to 30 wt. % and most particularly preferably from 1 to 15 wt. %, relative to the total amount of the ready-to-use agent.

Agents that are preferred according to the present specification are characterized in that the agent additionally includes at least one zwitterionic surfactant. Preferred zwitterionic surfactants are betaines, N-alkyl-N,N-dimethylammonium glycinates, N-acyl aminopropyl-N,N-dimethylammonium glycinates, and 2-alkyl-3-carboxymethyl-3-hydroxyethyl imidazolines. A preferred zwitterionic surfactant is known under the INCI name Cocamidopropyl Betaine.

Agents that are preferred according to the present specification are characterized in that the agent additionally includes at least one amphoteric surfactant. Preferred amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids. Particularly preferred amphoteric surfactants are N-cocoalkyl aminopropionate, cocoacylaminoethyl aminopropionate and $C_{12}$-$C_{18}$ acyl sarcosine.

It has also proved advantageous for the agents to include further, non-ionogenic interfacially-active substances. Preferred non-ionic surfactants are alkyl polyglycosides as well as alkylene oxide addition products with fatty alcohols and fatty acids, each including 2 to 30 mol of ethylene oxide per mol of fatty alcohol or fatty acid. Preparations having outstanding properties are likewise obtained if they include fatty acid esters of ethoxylated glycerol as non-ionic surfactants.

The non-ionic, zwitterionic or amphoteric surfactants are used in an amount of from 0.1 to 45 wt. %, preferably from 1 to 30 wt. % and most particularly preferably from 1 to 15 wt. %, relative to the total amount of the ready-to-use agent.

Agents that are suitable according to the present specification may also include cationic surfactants of the quaternary ammonium, esterquat and amidoamine types. Preferred quaternary ammonium surfactants are ammonium halides and the imidazolium compounds known under the INCI names Quaternium-27 and Quaternium-83. Further cationic surfactants which may be used according to the present specification are the quaternized protein hydrolysates. A compound from the amido amines that is particularly suitable according to the present specification is stearamidopropyl dimethylamine, which is commercially available under the name Tegoamid® S 18. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. The cationic surfactants are preferably included in the agents used according to the present specification in an amount of from 0.05 to 10 wt. %, relative to the total agent.

The ready-to-use coloring agents may include further auxiliary substances and additives. It has thus proved advantageous for the agents to include at least one thickening agent that is different from the agents of the first subject matter of the present specification. There are no restrictions in principle regarding these thickening agents. Both organic and also purely inorganic thickening agents may be used.

Suitable thickening agents that differ from the anionic polymers of the first subject matter of the present specification are cationic, synthetic polymers; naturally occurring thickening agents, such as non-ionic guar gums, scleroglucan gums or gum arabic, ghatti gum, karaya gum, tragacanth gum, carrageen gum, carob seed meal, pectins; starch fractions and derivatives such as amylose, amylopectin and dextrins; as well as non-ionic cellulose derivatives, such as for example methyl cellulose and hydroxyalkyl celluloses; non-ionic, fully synthetic polymers, such as polyvinyl alcohol or polyvinylpyrrolidinone; as well as inorganic thickening agents, in particular phyllosilicates, such as for example bentonite, particularly smectites, such as montmorillonite or hectorite.

Coloring processes on keratin fibers conventionally take place in an alkaline environment. In order to protect the keratin fibers and also the skin as far as possible, it is not desirable to establish too high a pH, however. The pH of the agents according to the present specification may therefore be between 3 and 11. It is preferable for the pH of the ready-to-use agent to be between 7 and 11, in particular between 8 and 10.5. The pH values in the context of the present specification are pH values measured at a temperature of 22 degrees Celsius (° C.).

The alkalizing agents which may be used according to the present specification to establish the preferred pH may be selected from the group formed from ammonia, alkanolamines, basic amino acids, as well as inorganic alkalizing agents such as alkaline-earth/alkali metal hydroxides, alkaline-earth/alkali metal metasilicates, alkaline-earth/alkali metal phosphates and alkaline-earth/alkali metal hydrogen phosphates. Preferred inorganic alkalizing agents are magnesium carbonate, sodium hydroxide, potassium hydroxide, sodium silicate and sodium metasilicate. Organic alkalizing agents that may be used according to the present specification are preferably selected from monoethanolamine, 2-amino-2-methylpropanol and triethanolamine. The basic amino acids that may be used as the alkalizing agent according to the present specification are preferably selected from the group formed from arginine, lysine, ornithine and histidine, particularly preferably arginine. In the context of the investigations leading to the present disclosure it has however been found that preferred agents according to the present specification are furthermore characterized in that they additionally include an organic alkalizing agent. One example of the first subject matter of the present specification is characterized in that the agent additionally includes at least one alkalizing agent which is selected from the group formed from ammonia, alkanolamines and basic amino acids, in particular from ammonia, monoethanolamine and arginine or the acceptable salts thereof.

It has furthermore proved advantageous for the coloring agents, in particular if they additionally include hydrogen peroxide, to include at least one stabilizer or complexing agent. Particularly preferred stabilizers are phenacetin, alkali benzoates (sodium benzoate) and salicylic acid. All prior art complexing agents may also be used. Preferred complexing agents according to the present specification are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

In a further preferred example the effect of the agent according to the present specification may be increased by means of emulsifiers. Such emulsifiers are for example

- addition products of 4 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid monoesters and diesters of addition products of 1 to 30 mol of ethylene oxide with polyols having 3 to 6 carbon atoms, in particular with glycerol,
- ethylene oxide and polyglycerol addition products with methyl glucoside fatty acid esters, fatty acid alkanolamides and fatty acid glucamides,
- $C_8$-$C_{22}$ alkyl mono- and oligoglycosides and ethoxylated analogs thereof, wherein degrees of oligomerization range from 1.1 to 5, in particular from 1.2 to 2.0, and glucose as the sugar component are preferred,
- mixtures of alkyl (oligo)glucosides and fatty alcohols, for example the commercially available product Montanov® 68,
- addition products of 5 to 60 mol of ethylene oxide with castor oil and hydrogenated castor oil,
- partial esters of polyols having 3 to 6 carbon atoms with saturated fatty acids having 8 to 22 carbon atoms,
- sterols, wherein sterols are understood to be a group of steroids which bear a hydroxyl group on carbon 3 of the steroid skeleton and are isolated from both animal tissue (zoosterols) and vegetable fats (phytosterols). Examples of zoosterols are cholesterol and lanosterol. Examples of suitable phytosterols are ergosterol, stigmasterol and sitosterol. Sterols known as mycosterols are also isolated from fungi and yeasts,
- phospholipids, above all glucose phospholipids, which are obtained for example as lecithins or phosphatidylcholines from various sources, such as egg yolk or plant seeds (e.g. soybeans),
- fatty acid esters of sugars and sugar alcohols, such as sorbitol,
- polyglycerols and polyglycerol derivatives such as for example polyglycerol poly-12-hydroxystearate (commercial product Dehymuls® PGPH),
- linear and branched fatty acids having 8 to 30 carbon atoms and Na, K, ammonium, Ca, Mg and Zn salts thereof.

The agents according to the present specification preferably include the emulsifiers in an amount of from 0.1 to 25 wt. %, in particular from 0.5 to 15 wt. %, relative to the total amount of the ready-to-use agent. Non-ionogenic emulsifiers or surfactants having an HLB (hydrophilic-lipophilic balance) value of 10 to 15 may be particularly preferred according to the present specification. Of the specified emulsifier types, emulsifiers that do not include ethylene oxide and/or propylene oxide in the molecule may be most particularly preferred.

The agents according to the present specification may also include further active ingredients, auxiliary agents and additives, such as for example non-ionic polymers, such as for example vinylpyrrolidinone/vinyl acrylate copolymers, polyvinylpyrrolidinone, vinylpyrrolidinone/vinyl acetate copolymers, polyethylene glycols and polysiloxanes; additional silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol; zwitterionic and amphoteric polymers; structuring agents such as glucose, maleic acid and lactic acid, hair-conditioning compounds such as phospholipids, for example lecithin and cephalins; perfume oils, dimethyl isosorbide and cyclodextrins; active ingredients to improve the fiber structure, in particular mono-, di- and oligosaccharides such as for example glucose, galactose, fructose, fruit sugars and lactose; dyes for coloring the agent; anti-dandruff active ingredients such as piroctone olamine, zinc omadine and climbazole; amino acids and oligopeptides; protein hydrolysates of animal and/or plant origin as well as those in the form of their fatty acid condensation products or optionally anionically or cationically modified derivatives thereof; vegetable oils; light stabilizers and UV blockers; active ingredients such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, pro-vitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, $CO_2$ and air.

Further substances may be selected in accordance with the desired properties of the agents. With regard to further optional components and to the amounts of these components used, reference is expressly made to the relevant manuals, for example Kh. Schrader, Grundlagen and Rezepturen der Kosmetika [Fundamentals and formulations of cosmetics], $2^{nd}$ Edition, Hüthig Buch Verlag, Heidelberg, 1989. The additional active ingredients and auxiliary substances are used in the agents according to the present specification preferably in amounts of from 0.0001 to 25 wt. % in each case, in particular from 0.0005 to 15 wt. %, relative to the total weight of the application mixture.

A method for coloring keratinic fibers, in particular human hair, which is characterized in that an agent of the first subject matter of the present specification is applied to the keratin-containing fibers, left on the fibers for from 5 to 60 minutes and then rinsed out again with water or washed out with a shampoo, is suitable in particular for the application of the agents according to the present specification. The contact time of the ready-to-use coloring agents is preferably from 5 to 45 minutes, in particular from 10 to 40 minutes, particularly preferably from 15 to 35 minutes. During the contact time of the agent on the fibers, it may be advantageous to support the lightening process by supplying heat. Heat may be supplied both from an external heat source, such as for example hot air from a hot air blower, and also, in particular if the hair lightening process is taking place on a living test subject, from the body temperature of the test subject. In the latter case the section to be lightened is conventionally covered with a hood. A contact phase at room temperature is likewise in accordance with the present specification. In particular, the temperature during the contact time is between 20° C. and 40° C., in particular between 25° C. and 38° C. After the end of the contact time the remaining coloring preparation is rinsed out of the hair with water or a cleaning agent. Commercial shampoo may be used in particular as the cleaning agent, wherein in particular if the lightening agent has a carrier having a high surfactant content, the cleaning agent may be dispensed with and the rinsing process may take place with water.

The agents according to the present specification may be formulated as one-component agents (coloring and lightening agent) or as multi-component agents such as two-component agents or three-component agents, and used accordingly. A separation into multi-component systems is useful in particular where incompatibilities between the ingredients are to be expected or of concern; in such systems, the agent to be used is prepared by the consumer immediately before use by mixing the components together.

If the agent according to the present specification includes both substantive dyes—as well as optionally additionally oxidation dye precursors—and oxidizing agents, they are conveniently packaged separately from one another in order to avoid a premature, undesired reaction and brought into contact only immediately before application.

A coloring and lightening method in which the coloring cream and the oxidizing agent are initially separate is therefore preferred. The present specification therefore also provides a method for coloring and lightening human hair, wherein a composition on an aqueous basis including hydrogen peroxide is mixed with an agent according to the present specification including at least one compound of formula (I) to form a homogeneous composition, and this is applied to the hair. The anionic polymer (b) may in this case be packaged with the hydrogen peroxide solution, with the compound of formula (I), or with both.

In a further example of the present specification, agents are therefore preferred which are characterized in that they are produced immediately before application by mixing at least two preparations, wherein the at least two preparations are provided in at least two separately packaged containers, and wherein one container contains an agent (A), which includes in a cosmetic carrier at least one cationic anthraquinone dye of formula (I), optionally including oxidation dye precursors as well, and a further container contains an oxidizing agent preparation (B) including at least one oxidizing agent. The anionic polymer (b) may in this case be packaged together with the cationic anthraquinone dye of formula (I) in container A, together with the oxidizing agent preparation in container (B), or both.

The formulation of a combination of (a) compounds of the general formula (I) with (b) special anionic polymers is outstandingly suitable for producing intense colors with high brilliance, high shine and a low selectivity in conjunction with an outstanding wash fastness.

The present specification also provides the use of an agent of the first subject matter of the present specification to produce hair dyes having increased shine, an intense color result with improved fastness properties and/or reduced selectivity.

All that has been stated with respect to the agents according to the present specification applies with necessary alterations to the further preferred examples of the methods and use according to the present specification.

EXAMPLES

The examples that follow indicate agents that were produced according to the present specification for the treatment of keratinous fibers. Unless otherwise indicated, the stated quantities are percentages by weight.

Formulation Example 1

| Description | wt. % |
|---|---|
| Coconut alcohol | 4.00 |
| Cocamidopropyl betaine, 40% | 4.00 |
| Sodium myreth sulfate (2 EO), 27% | 4.00 |
| Laureth-2 | 0.80 |
| Emulgade 1000 NI | 3.00 |
| Methylparaben | 0.15 |
| Propylparaben | 0.19 |
| Polyethylene glycol MG 400 | 3.00 |
| Acid Red 33 | 0.005 |
| N-(2-Hydroxyethyl)-4-methyl-2-nitroaniline (Methyl Yellow) | 0.04 |
| Carbomer [1000-7000 mPas (0.2%)] | 0.50 |
| Monoethanolamine | 0.23 |
| 1,3-Butanediol | 1.00 |
| Water, demineralized | 3.00 |
| Polyquaternium-6 | 0.50 |
| Cationic Blue 347 | 0.20 |
| Perfume | qs |
| Water | to 100 |

Formulation Example 2

| Description | wt. % |
|---|---|
| Methylparaben | 0.10 |
| Carbomer [20000-30000 mPas (0.2%)] | 0.20 |
| KOH, 50% | 0.10 |
| Jaguar C-17 | 0.70 |
| Genamin KDMP | 3.00 |
| Cetearyl alcohol + PEG-20 stearate | 2.50 |
| Cetearyl alcohol | 3.00 |
| Liquid paraffin | 2.00 |
| Emulgade 1000 NI | 2.40 |
| Genamin CTAC | 3.00 |
| Acid Violet 43 | 0.008 |
| Cationic Blue 347 | 0.20 |
| Prestige Bright Mystic Violet | 0.12 |
| Prestige Amethyst | 0.11 |
| Prestige Fire-Red | 0.012 |
| KH$_2$PO$_4$ | 0.30 |
| Benzophenone-4 | 0.10 |
| D-Panthenol, 75% | 1.00 |
| Dimethicone/Dimethiconol | 2.00 |
| Phenoxyethanol | 0.40 |
| Crodarom Rock Crystal | 1.00 |
| Methylisothiazolone, approx. 10% in H$_2$O | 0.10 |
| Perfume | qs |
| Water | to 100 |

Recipe Constituents
Cationic Blue 347 3-[(4-amino-9,10-dihydro-3-methyl-9,10-dioxo-1-anthracenyl)amino]-N,N,N-trimethyl-1-propan-aminium methosulfate,
Emulgade 1000 NI INCI name: Cetearyl alcohol, Ceteareth-20 (BASF)
Jaguar C-17 INCI name: Guar Hydroxypropyltrimonium Chloride (Rhodia)
Genamin KDMP approx. 80% active content; INCI name: Behentrimonium Chloride, Isopropanol (Clariant)
Genamin CTAC approx. 29% active content; INCI name: Aqua, Cetrimonium Chloride (Clariant)
Emulgade 1000 NI INCI name: Cetearyl alcohol, Ceteareth-20 (BASF)
Prestige Bright Mystic Violet INCI name: Mica, CI 77491 (Iron Oxides), Tin Oxide (Eckart Cosmetic Colours)
Prestige Amethyst INCI name: Mica, CI 77891 (Titanium Dioxide), Tin Oxide, CI 77510 (Ferric Ferrocyanide), CI 75470 (Carmine) (Eckart Cosmetic Colours)
Prestige Fire-Red INCI name: Mica, CI-77491 (Iron Oxides) (Eckart Cosmetic Colours)
Crodarom Rock Crystal INCI name: Aqua, Propylene Glycol, Quartz (Crodarom)

The coloring formulations were applied to hair strands and left there for 30 minutes at room temperature. Then the fibers were rinsed thoroughly with water and dried. The treated fibers were characterized by intense colors with high shine and an outstanding wash fastness.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability or configuration of the invention in any way. Rather, the foregoing detailed description will provide those skilled in the art with a convenient road map for implementing an exemplary embodiment of the invention, it being understood that various changes may be made in the function and arrangement of the elements described in an exemplary embodiment without departing from the scope of the invention as set forth in the appended claims and their legal equivalents.

The invention claimed is:

1. An agent for coloring keratinic fibers comprising, in a cosmetic carrier,
(a) at least one compound of formula (I):

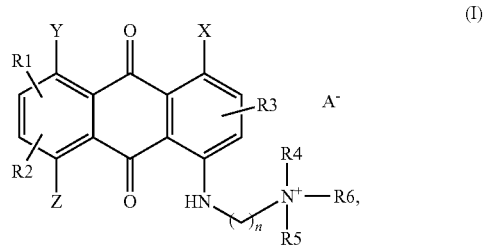

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, C$_1$-C$_6$ alkoxy group, a C$_2$-C$_6$ alkenyl group, a C$_2$-C$_6$ hydroxyalkyl group or a C$_1$-C$_6$ alkoxy C$_2$-C$_6$ alkyl group;
in which
at least one of the R1, R2 and R3 denotes a halogen, a carboxyl group, a sulfonic acid group, a C1-C6 alkyl group or a C1-C6 alkoxy group;
R4, R5, R6 each independently of one another, denote a C$_1$-C$_6$ alkyl group, a C$_2$-C$_6$ alkenyl group, a C$_2$-C$_6$ hydroxyalkyl group or a C$_1$-C$_6$ alkoxy C$_2$-C$_6$ alkyl group;
or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen, a hydroxyl group or an N(R7)(R8) group,
in which:
R7 and R8, each independently of one another, denote hydrogen, a C$_1$-C$_6$ alkyl group, a C$_2$-C$_6$ alkenyl group, a C$_2$-C$_6$ hydroxyalkyl group or a C$_1$-C$_6$ alkoxy C$_2$-C$_6$ alkyl group;
wherein at least one of the residues X, Y and Z denotes an N(R7)(R8) group;
n denotes an integer between 2 and 6 inclusive; and
A⁻ denotes a physiologically acceptable anion;
and
(b) from 0.001 to 15 wt. %, relative to the total weight of the agent, of at least one anionic polymer.

2. The agent of claim 1, wherein the agent simultaneously lightens the keratinic fibers.

3. The agent of claim 1, wherein X of formula (I) denotes an NH$_2$ group and at least one of R4, R5 and R6 of formula (I) denotes a propyl group.

4. The agent of claim 1, wherein the compound of formula (I) is provided by a compound according to formula (Ia),

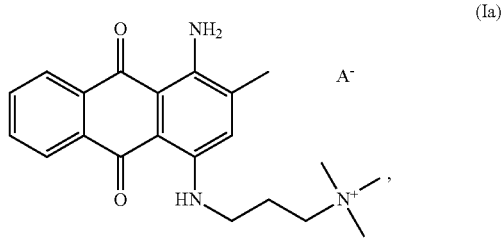

(Ia)

in which A⁻ denotes a physiologically acceptable anion.

5. The agent of claim 1, wherein the compound(s) according to formula (I) comprise an amount of from 0.0001 to 5 wt. %, relative to the total weight of the agent.

6. The agent of claim 1, wherein the compound(s) according to formula (I) comprise an amount of from 0.005 to 3.5 wt. %, relative to the total weight of the agent.

7. The agent of claim 1, wherein the compound(s) according to formula (I) comprise an amount of from 0.01 to 2.5 wt. %, relative to the total weight of the agent.

8. The agent of claim 1, wherein the anionic polymer (b) is selected from the group consisting of:
(i) polymers of acrylic acid, methacrylic acid, or combinations thereof;
(ii) polymers of 2-acrylamido-2-methyl-1-propanesulfonic acid;
(iii) anionic polysaccharides;
(iv) polymers of itaconic acid
(v) polymers of crotonic acid;
(vi) polymers of maleic anhydride; and
(vii) combinations thereof.

9. The agent of claim 1, wherein the anionic polymer(s) (b) comprise an amount of from 0.5 to 5.0 wt. %, relative to the total weight of the agent.

10. The agent of claim 1, wherein the anionic polymer(s) (b) comprise an amount of from 0.05 to 12 wt. %, relative to the total weight of the agent.

11. The agent of claim 1, wherein the anionic polymer(s) (b) comprise an amount of from 0.1 to 10.0 wt. %, relative to the total weight of the agent.

12. The agent of claim 1, wherein the anionic polymer (b) comprises at least one polymer selected from the group consisting of:
Carbomer (polyacrylic acid);
Sodium Polyacrylate;
Sodium Acrylate/Sodium Acryloyldimethyl Taurate Copolymer;
Acrylates/C10-30 Alkyl Acrylate Crosspolymer;
Acrylates/Steareth-20 Methacrylate Crosspolymer;
Acrylates/Palmeth-25 Acrylate Copolymer;
Acrylates/Palmeth-20 Acrylate Copolymer;
Acrylates Copolymers;
Acrylates/Steareth-20 Methacrylate Copolymer; and
combinations thereof.

13. The agent of claim 1, wherein the anionic polymer (b) comprises at least one polymer selected from the group consisting of:
xanthan (xanthan gum);
alginate (algin);
carboxymethylcellulose or a physiologically acceptable salt thereof;
hyaluronic acid or a physiologically acceptable salt thereof; and
combinations thereof.

14. The agent of claim 1, further comprising at least one additional substantive dye, in addition to the dye of formula (I).

15. The agent according to claim 14, wherein the at least one additional substantive dye is selected from the group consisting of: D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxethyl)-4-methyl-2-nitroaniline (Methyl Yellow), HC Yellow No. 2, Red B 54,2-amino-6-chloro-4-nitrophenol, and combinations thereof.

16. The agent of claim 1, further comprising hydrogen peroxide or a solid addition product thereof with organic or inorganic compounds.

17. The agent of claim 1, further comprising at least one zwitterionic surfactant selected from the group consisting of N-alkyl-N,N-dimethylammonium glycinates, N-acyl aminopropyl-N,N-dimethylammonium glycinates, 2-alkyl-3-carboxymethyl-3-hydroxyethyl imidazolines, and combinations thereof.

18. The agent of claim 1, further comprising the zwitterionic surfactant cocamidopropyl betaine.

19. A method of dyeing keratinic fibers to produce increased shine, an intense color result with improved fastness properties or reduced selectivity, comprising:
(A) applying an agent for coloring, and optionally simultaneously lightening, keratinic fibers, comprising, in a cosmetic carrier, (i) at least one compound of formula (I):

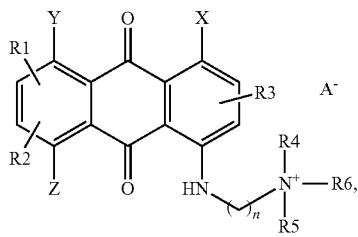

(I)

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
in which
at least one of the R1, R2 and R3 denotes a halogen, a carboxyl group, a sulfonic acid group, a C1-C6 alkyl group or a C1-C6 alkoxy group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen, a hydroxyl group or an N(R7)(R8) group,
in which:
R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group,
wherein at least one of the residues X, Y and Z denotes an N(R7)(R8) group;
n denotes an integer between 2 and 6 inclusive; and
$A^-$ denotes a physiologically acceptable anion;
and
(ii) from 0.001 to 15 wt. %, relative to the total weight of the agent, of at least one anionic polymer; and (B) after a contact time, rinsing the agent from the keratinic fibers.

20. An agent for coloring keratinic fibers comprising, in a cosmetic carrier,
(a) at least one compound of formula (I):

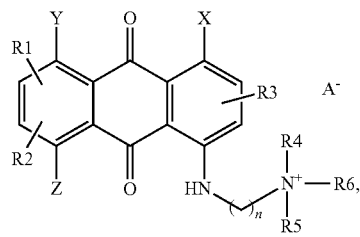

(I)

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen, a hydroxyl group or an N(R7)(R8) group,
in which:
R7 and R8 are the same as one another, and denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
wherein at least one of the residues X, Y and Z denotes an N(R7)(R8) group;
n denotes an integer between 2 and 6 inclusive; and
$A^-$ denotes a physiologically acceptable anion;
and
(b) from 0.001 to 15 wt. %, relative to the total weight of the agent, of at least one anionic polymer.

\* \* \* \* \*